United States Patent [19]

Stocker et al.

[11] Patent Number: 4,849,403

[45] Date of Patent: Jul. 18, 1989

[54] PROTEIN C ACTIVATOR, METHODS OF PREPARATION AND USE THEREOF

[75] Inventors: Kurt F. Stocker, Aesch; Lars G. Svendsen, Reinach, both of Switzerland

[73] Assignee: Pentapharm AG, Basel, Switzerland

[21] Appl. No.: 861,786

[22] Filed: May 9, 1986

[30] Foreign Application Priority Data

May 29, 1985 [CH] Switzerland ............................ 2267/85
Sep. 25, 1985 [CH] Switzerland ............................ 4135/84
Nov. 28, 1985 [CH] Switzerland ............................ 5087/85

[51] Int. Cl.$^4$ ............................................. A61K 37/00
[52] U.S. Cl. ............................................ 514/2; 424/98; 435/23; 435/24; 435/68; 435/172.1; 530/381
[58] Field of Search ................. 435/23; 530/381; 424/98; 514/2

[56] References Cited

PUBLICATIONS

Exner et al.–Chem. Abst., vol. 104 (1986) p. 47533g.
Stocker et al.–Chem. Abst., vol. 105 (1986) p. 74085q.
Moran et al.–Comp. Biochem. Physiol. B, vol. 70B (2)(1981)pp. 349–351.
Moran et al.–Chem. Abst., vol. 96 (1982) p. 64662q.

*Primary Examiner*—Sam Rosen
*Attorney, Agent, or Firm*—Pennie & Edmonds

[57] ABSTRACT

A method and composition for assaying protein C is described. The method comprises reacting a protein C-containing medium with a protein C-activating activator preparation obtained from venom of the snake Agkistrodon contortrix, or venom of another snake species which undergoes an immunological cross-reaction with the venom of Agkistrodon contortrix, to cause maximum activation of protein C and subsequently determining the quantity of activated protein C, said quantity being proportional to the amount of protein C in said medium. Also disclosed is a method and composition for treating thrombotic disorders with the activator preparation and a method of obtaining the activator preparation by culturing of a cloned microorganism.

18 Claims, 1 Drawing Sheet

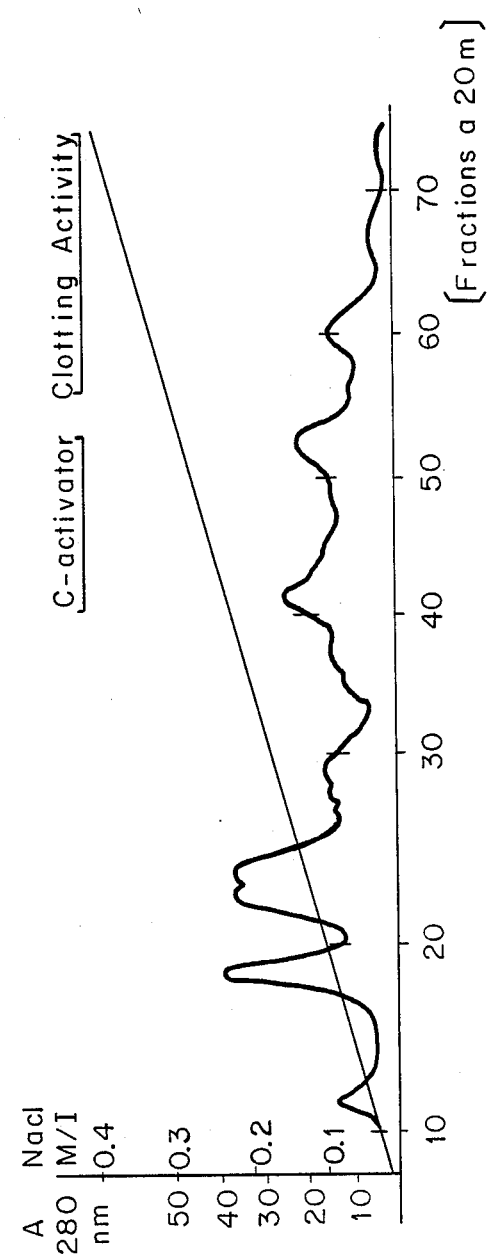

PROTEIN C ACTIVATOR, METHODS OF PREPARATION AND USE THEREOF

The present invention relates to a method for quantitatively assaying the zymogen protein C, as well as an activator preparation for applying this method.

Protein C is a zymogen of the haemostatic system which is present in the blood plasma of men and mammals and which is activated into the serine proteinase protein $C_a$ by a complex of thrombin and the insoluble protein of the vascular wall thrombomodulin. Protein $C_a$ causes on one hand the hydrolytic degradation of the clotting factors V (Accelerin) and VIII (antihaemophilic factor A) and on the other hand an activation of fibrinolysis. The action of protein C is potentiated by protein S, phospholipid and calcium and is inhibited by a specific inhibitor contained in plasma.

Due to these properties and effects, protein C plays an essential role in the regulation of haemostasis; it prevents clotting in intact blood vessels without disturbing haemostasis at the site of a vascular injury.

Protein C is a glycoprotein with a molecular weight of about 60,000 which is synthesized in the liver in dependence of vitamin K. Its molecule contains several γ-carboxyglutamic acid residues which are necessary for binding calcium and for forming the enzyme-phospholipid complex. An anticoagulant therapy with vitamin K-antagonists leads to the synthesis of acarboxy protein C which has an enzymatic activity too, but cannot be potentiated by phospholipid and calcium.

Congenital or acquired lack or molecular malformations of protein C lead to an increased thrombosis tendency in men.

Detailed descriptions of protein C can be found in KISIEL, W. and DAVIE, E. W. Protein C, Methods in Enzymology 80, 320-332 (1981) and WITT, I. Protein C-Ein neuer Faktor der Haemostase. In: L. Roka and E. Spanuth (Eds.) Neue Aspekte in der Gerinnungsdiagnostik p. 1-16 (1984) Stuttgart, New York: Schattauer Verlag.

Due to the antigenic properties of protein C, its quantitative assay according to an immunological technique is possible.

According to the enzyme-linked immunoadsorption method (ELISA, cf. I. WITT, loc. cit.), the protein C assay consists in preparing a specific antibody directed against protein C by immunization of rabbits, in binding it to a plastic support and in bringing the sample into contact with the antibody-coated support, whereby the antigen "protein C" is bound by the antibody. Then, peroxidase-coupled antibody is added in excess and binds to the still available, free antigenic determinants of the adsorbed protein C. After removal of the excessive, labelled antibody, the activity of peroxidase linked by immunoadsorption is determined by means of ophenylenediamine. The activity of linked peroxidase is proportional to the protein C concentration in the sample. A test combination for the protein C assay according to the ELISA technique is commercially available (ELISA-protein C, Boehringer Mannheim, FRG).

According to an immunoelectrophoretic method (R. M. BERTINA, Thrombosis & Haemostasis 48 (1), 1-5 (1982)), the antibody directed against protein C is added to an agarose solution, a plate is moulded thereof and the sample is applied on the antibody plate which is put under direct current in an appropriate device for several hours. Thereafter non-precipitated protein is rinsed out from the gel plates and the resulting rocket-like precipitine areas are revealed by staining with amido black. The length of the precipitine areas is proportional to the protein C concentration in the sample. Pre-coated antibody plates for the protein C assay, such as "Assera ®-Plate Protein C", Diagnostica Stago, Asnières, France, are commercially available.

Moreover, protein C can also be assayed according to a radioimmunological method by labelling the specific anti-protein C-antibody with a radioactive isotope, such as $^{125}I$ for example, and by radiologically measuring its linkage to protein C in the sample. A radioimmunological method for assaying protein C has been described by K. IKEDA and J. STENFLO in Thrombosis Research 39, 297-306 (1985).

However, the said immunological methods for assaying protein C bear several disadvantages. First, highly purified preparations of protein C are required for obtaining the specific antibody since an impurity of the antigen due to plasma proteins would lead to an antibody having a too broad binding capability which would simulate erroneously high protein C concentrations in the sample. Moreover, immunological methods require so much work, devices and time that they are only applicable when on one hand the patient's state justifies this complicated technique and on the other hand when a long waiting-period for th4e results is allowed. Finally, the diagnostic significance of immunological protein C assays is limited since, besides, activable, enzymatically functional protein C, these methods also measure its pathologic forms as well as consumed, inhibitor-linked, inactivated enzyme.

The complicated purification of protein C as well as the manufacture of antibody preparations are unnecessary and the assay becomes specific to functional protein C if it can be measured not on its antigenic properties but on its enzyme activity.

Protein C can be functionally assayed by activating the zymogen and by measuring the resulting enzyme activity on a natural or synthetic substrate.

According to KISIEL and DAVIE's method (KISIEL, W. and DAVIE, E. W. Protein C. Methods in Enzymology 80, 320-332 (1981)), protein C is assayed in chromatographic fractions using the kaolin-cephalin clotting time of human citrated plasma as the indicator reaction. In a first step, the protein C-containing sample is activated by incubation with thrombin for 30-60 minutes and the excess of thrombin is then neutralized by addition of antithrombin III and heparin. In a second step, normal plasma is added to an aliquot of the activation mixture, the clotting system is activated by addition of calcium chloride, cephalin and kaolin and the time until coagulation is measured. The degradation of factors V and VIII caused by activated protein C leads to a prolongation of the clotting time as compared to a control test without protein C; this prolongation is proportional to the protein C content of the sample.

Although this method specifically measures the functional protein C, it can only be applied for inhibitor-free protein C preparations as the protein C inhibitor contained in plasma inactivates the enzyme more rapidly than it is formed by thrombin activation.

According to FRANCIS and PATCH's method (R. B. FRANCIS and M. J. PATCH. A functional assay for protein C in human plasma. Thromb. Res. 32, 605-613 (1983)), the interference of the protein C inhibitor is eliminated by treating the sample, respectively the patient's plasma to be examined, with barium citrate in order to adsorb protein C while the inhibitor remains in solution. By treatment with sodium morpholinoethylsulphate, the protein C is eluted from the centrifuged adsorbate, washed and partially activated through incubation with α-thrombin for 60 minutes. Thereafter, thrombin is inactivated with antithrombin III and heparin, and heparin is then neutralized with protamine sulphate. The protein C activity in the sample prepared in this way is then determined on human normal plasma by measuring the prolongation of the kaolin-cephalin clotting time.

A calibration curve is established by means of the dilution series of normal plasma and the obtained clotting times, from which the protein C content in the patient's plasma may be read in percent of the norm.

The main disadvantages of FRANCIS and PATCH's method are its complexity and the long incubation time with thrombin which, nevertheless, does not lead to a total activation of the present protein C quantity, which in fact would require 4 hours of incubation at 37° C. with the applied test procedure.

The paper of BERTINA et al. (R. M. BERTINA, A. W. BROEKMANS, C. KROMMENHOEK-van ES and A. van WYJNGAARDEN discusses the use of a functional and immunological assay for plasma protein C in the study of the heterogeneity of congenital protein C deficiency. Thrombosis and Haemostasis 51, 1–5 (1984)) describes a method for assaying protein C in patients' plasma, wherein the direct splitting of a chromogenic substrate is used instead of the complicated inhibition of the kaolin-cephalin clotting time as the indicator reaction. According to this method, protein C is separated from the patients' plasma by adsorption on aluminium hydroxide and elution with ethylenediaminetetraacetic acid, activated 45 minutes at 37° C. with thrombin, thrombin is inhibited with anti-thrombin III and heparin and finally, the activated protein C is assayed by measuring the p-nitroaniline release from the synthetic chromogenic substrate pyroglutamyl-L-prolyl-L-arginine-p-nitroanilide.

The adsorption step described in all methods for the functional protein C assay in plasma and the activation by thrombin affect the accuracy and rapidity of the assay.

Adsorption and elution are non-quantitative temperature- and time-dependent processes which require standardized performance by adequately trained staff. In addition, the substances used for elution modify the electrolyte composition of the test medium and influence thereby the substrate hydrolysis.

Thrombin activates protein C slowly and uncompletely and has to be inhibited with antithrombin III and heparin or hirudin after accomplished activation in order to avoid its reaction with the substrate and, if using a natural substrate, to avoid the obtainment of erroneously low or, if using a synthetic substrate, of erroneously high protein C concentrations. However, to prevent that added antithrombin and heparin themselves prolong the kaolin-cephalin clotting time and cause erroneously high results, heparin has to be neutralized with protamine sulphate if protein C has to be assayed according to a clotting method. Moreover, the use of thrombin as the activator for photometrically assaying protein C implies that the chromogenic substrate used for measuring the protein C activity cannot or only to a very small extent be split by thrombin itself.

No practically usable, better alternatives to the protein C activation with thrombin are known up to now.

Activation with thrombin is strongly accelerated by thrombomodulin, but this water-insoluble protein is not yet available in a ready-for-use form.

An also accelerating addition of calcium is impossible in plasma as, thereby, the clotting system and thus other proteinases than protein C would be activated, which would then themselves react with the natural or synthetic substrate.

Although the factor X-activator isolated from the venom of the Russell viper has been demonstrated by KISIEL and DAVIE to exert an activating effect on protein C, it cannot be applied for a protein C assay because its action is even slower than the one of thrombin. Trypsin, which also causes a proteolytic activation of protein C, cannot be used since, as an unspecific proteinase, it activates and inactivates a great number of other plasma zymogens and moreover, it reacts with the substrates used.

Proteinases with a thrombin-like substrate specificity, such as the fibrinopeptide A-releasing batroxobin from the venom of Bothrops atrox or Ancrod from the venom of Agkistrodon rhodostoma, the fibrinopeptide B-releasing enzyme from the venon of Agkistrodon contortrix, the thrombocyte-activating enzyme thrombocytin from the venom of B. atrox, do not activate protein C, and thrombin coagulase formed from prothrombin by staphylocoagulase or meizothrombin formed from prothrombin by ecarin display similar properties as thrombin and therefore do not present any advantage.

However, it could be surprisingly found that a protein from the venom of the Copperhead Agkistrodon contortrix, which exerts no thrombin-like action on fibrinogen and thrombocytes, which in contrast to thrombin splits neither fibrinopeptide A nor B from fibrinogen and which triggers neither aggregation nor release reactions on thrombocytes, causes a very strong and rapid activation of purified protein C. It has been found in addition that this snake venom protein is capable of activating protein C in so highly diluted plasma that the present protein C-inhibitor has practically no action or that an activation product is formed which is not inhibited by the plasma protein C-inhibitor, a complicated separation of protein C and inhibitor by adsorption being thereby unnecessary. Moreover, it has been found that the protein C-activating snake venom protein exerts no demonstrable proteinase activity and thereby affects neither a natural nor a synthetic substrate. Conversely, thrombin exerts a splitting action on synthetic substrates as well as a clotting action on natural substrates, which leads to the necessity to add an accurately weighed quantity of a specific inhibitor in order to abolish the undesired action of thrombin. It has been finally found that this activator is capable of activating protein C so quickly that a functional assay of protein C with usual automatic devices becomes possible.

The present invention relates to a method for assaying protein C in a medium containing same, which comprises reacting the said medium with venom of the snake Agkistrodon contortrix, or venom of another snake species which undergoes an immunological cross-reaction with the venom of Agkistrodon contortrix, or a protein C-activating activator preparation obtained from one of the said venoms for a period of time sufficient to cause maximum activation of the zymogen protein C to a proteinase having protein $C_a$-activity and determining the quantity of activated protein C thus formed either by photometrically measuring the quantity of coloured or fluorescent split product formed as a result of the catalytic hydrolytic action of activated protein C on a synthetic chromogenic substrate, or by measuring the prolongation of the clotting time of a natural substrate caused by activated protein C, or which comprises adding to the said medium a synthetic chromogenic substrate and the said venom or the said activator preparation, following photometrically the hydrolytic release of the coloured or fluorescent split product from the said substrate and calculating the protein C content in the said medium from the observed maximum velocity of the substrate hydrolysis.

The specificity of protein C activation in human citrated plasma was verified by means of specific proteinase substrates and inhibitors as well as by measurements on various clotting factor-deficient plasmas. By incubating plasma with the activator preparation of the invention, no enzymes, which split the plasma kallikrein substrate Bz—L—Pro—L—Phe—L—Arg—pNA, the factor $X_a$ substrate $CH_3$—$SO_2$—D—Leu—Gly—L—Arg—pNA or the plasmin substrate Tos—Gly—L—Pro—L—Lys—pNA, are activated. By measurements on the chromogenic substrates H—D—CHG—L—Pro—L—Arg—pNA and H—D—Pro—L—Pro—L—Arg—pNA, amidolytic activities in the same order of magnitude are found after activation with the activator preparation of the invention in normal plasma and in plasma deficient in factors VII, XI or X respectively while in protein C-free human plasma the activator preparation of the invention produces no activity splitting the protein C-substrates 2AcOH—H—D—Pro—L—Pro—L—Arg—pNA and 2AcOH—H—D—Lys(Cbo)—L—Pro—L—Arg—pNA. Measured on the chromogenic substrate H—D—Pro—L—Pro—L—Arg—pNA, the protein C activity generated by the activator of the invention from plasma is not inhibited by addition of the specific thrombin inhibitor hirudin or by addition of the polyvalent human urinary trypsin inhibitor. Addition of the polyvalent proteinase inhibitor aprotinin to plasma before incubation with the protein C activator of the invention totally prevents the chromogenic protein C substrates from hydrolysis. Addition of aprotinin after accomplished activation and during ongoing substrate hydrolysis inhibits the reaction immediately and totally. Accordingly, purified human protein C activated with insolubilized thrombin is also completely inhibited by aprotinin. These results prove that the activator of the invention specifically activates protein C and that it thereby leads neither to the formation of thrombin, plasmin, factor $X_a$ and plasma kallikrein nor to the formation of another enzyme activity affecting the chromogenic protein $C_a$ substrates. Moreover, the accuracy of the protein C assay in plasma using the activator of the invention and a chromogenic substrate could be proven by increasing the physiological protein C level in plasma with added protein C. The protein C content found in that plasma corresponded to the sum of physiological concentration and added amount of protein C. Besides, the functionability of the method for assaying protein C of the invention could be proven by activity measurements in mixtures of protein C-free and normal human plasma as well as by activity measurements on normal human plasma with increasing additions of anti-protein C antibody.

The invention further concerns an activator preparation from snake venoms, which is capable of converting protein C from men and vertebrates, e.g. sheep, goat, cow, horse, pig, rabbit and hen, into activated protein C.

Venoms of solenoglyph snakes (i.e. those with mobile, canaliculated venom-fangs), which belong to the viper family (Viperidae), in particular to the tribe of the pit vipers (Crotalinae) and within this tribe to the genus Agkistrodon, are appropriate as raw materials for the manufacture of the protein C activator preparations of the invention. The venom of the species A. contortrix, that of its subspecies, such as A. contortrix contortrix, A. contortrix laticinctus, A. contortrix mokeson, A. contortrix phaeogaster, A. contortrix pictigaster, as well as venom of species which undergo an immunological cross-reaction with the venom of A. contortrix, such as A. piscivorus, that of its subspecies, such as A. piscivorus piscivorus, A. piscivorus conanti, A. piscivorus leucostoma, and venom of the species A. bilineatus and of its subspecies, such as A. bilineatus binineatus, A. bilineatus taylori and A. bilineatus russeolus, are particularly adequate.

A review on the zoological classification of the snake fauna can be found in G. UNDERWOOD, Classification and distribution of venomous snakes in the world. In: C. Y. LEE (Ed.) Snake venoms p. 15–40, Berlin, Heidelberg, New York: Springer-Verlag (1979); explanations about the immunological cross-reaction between venoms of different snake species and antibodies from the serum of immunized mammals can be found in S. A. MINTON, Common antigens in snake venoms, loc. cit., p. 847–862.

The isolation and purification of the protein C activator from snake venom can be performed by means of known methods for protein separation, such as fractionated ethanol or ammonium sulphate precipitations, high or low pressure chromatography on molecular filtration or ion exchanger systems, affinity chromatography, preparative electrophoresis, or by a combination of several of the said techniques. A topical view on the methods for protein separation can be found in R. SCOPES, Protein purification, New York, Heidelberg, Berlin: Springer-Verlag (1982).

The activator preparation of the invention may for instance be manufactured by chromatography of the above mentioned snake venom, e.g. A. contortrix venom, on an anion exchanger having the appropriate porosity for binding proteins, e.g. cross-linked diethylaminoethyldextran (DEAE-Sephadex ® A-50) or diethylaminoethylcellulose, elution with sodium phosphate buffer at neutral pH and increasing ionic strength, removal of electrolytes from the protein C-activating fractions by ultrafiltration and subsequent lyophilization.

Tested in a concentration of 2 µg per ml on human fibrinogen, the activator preparation manufactured in this way caused no clotting within 10 minutes and, tested on a non-heated human fibrin plate, no fibrinolysis within 15 hours.

Measured on the synthetic chromogenic substrate H—D—Pro—L—Pro—L—Arg—pNA, purified human protein C is activated by the activator preparation in a concentration of 2 µg of protein per ml of test mixture within at most 10 minutes at pH 8, ionic strength 0.15 and 37° C.

The protein C-activating action of the activator preparation is reduced neither by incubation with 2.5 µmoles of diisopropylfluorophosphate per 1 ml at pH 8 for 15 hours nor by incubation with 1 mg of iodoacetamide per 1 ml of pH 7 for 15 hours, nor by addition of 0.05 μmole of ethylenediaminetetraacetic acid disodium salt per 1 ml. Besides, the protein C-activating action of the activator preparation is inhibited neither by the thrombin inhibitors antithrombin III, heparin and hirudin nor by the polyvalent proteinase inhibitor aprotinin.

The activator preparation of the invention may also be obtained by dilution of the snake venom in an aqueous medium, removal of the undesired venom components from the solution either by fractionated alcohol precipitation, fractionated salt precipitation or heat treatment at an acid pH for the purpose of preparing a pre-purified venom fraction, further purification of the obtained pre-purified venom fraction by chromatography on an anion exchanger having the appropriate porosity for binding proteins, e.g. cross-linked diethylaminoethyldextran or diethylaminoethylcellulose, elution with sodium phosphate buffer at neutral pH and increasing ionic strength, further chromatography on a cation exchanger, e.g. cross-linked carboxymethyldextran or carboxymethylcellulose, elution with a sodium acetate buffer at an acid pH, concentration of the protein C-activating eluates by ultrafiltration, removal of electrolytes and final purification of the concentrate by chromatography on a molecular sieve gel, e.g. a cross-linked dextran gel, using diluted aqueous acetic acid as the eluent, and subsequent lyophilization.

The activator preparation manufactured in this way is characterized by the fact that, in a concentration of 0.1–0.5 μg per ml of aqueous reaction mixture at pH 6–8 and at a temperature of 20°–40° C., it causes maximum activation of the protein C present in 0.05 ml of normal human citrates plasma within at most 10 minutes, that, in a concentration of 5 μg per ml of test mixture, it causes neither coagulation of human fibrinogen within 10 minutes nor lysis of human fibrin within 15 hours, that it does not activate prothrombin and clotting factor X, that it generates no amidolytic activity from protein C-free plasma, that its protein C-activating action is not reduced by incubation with 2.5 μmoles of diisopropyl-fluorophosphate per 1 ml at pH 8 for 15 hours or by incubation with 1 mg of iodoacetamide per 1 ml at pH 7 or by additon of 0.05 μmole of ethylenediaminetetraacetic acid disodium salt per 1 ml, that its protein C-activating action is not inhibited by thrombin inhibitors such as antithrombin III, heparin and hirudin, or by the polyvalent proteinase inhibitor aprotinin, that it does not lose its protein C-activating action by heating to 70° C. at pH 3 to 8 for 10 minutes or by storage at 20°–25° C. at pH 2 to 8 for 24 hours, that it shows a significant decrease in activity after 1 hour at pH 9, that it loses its protein C-activating action after addition of 4% of sodium dodecylsulphate or 5 μmoles of manganese-II lactate per 1 ml, that treatment with dithiothreitol at pH 7 for 24 hours only slightly reduces its activity, that it is neutralized by polyvalent anti-American pit viper antiserum, that, after reduction with dithiothreitol and subsequent alkylation with iodoacetamide, it shows one single band with a relative electrophoretic mobility corresponding to a molecular weight of 39,000±3,000 in polyacrylamide gel electrophoresis in the presence of sodium dodecylsulphate and after staining with Coomassie blue, that it shows a sedimentation constant ($S20_w$) of 2.65±3% corresponding to the molecular weight of 36,800÷5% in the analytic ultracentrifugation, that it is eluted on a calibrated column of cross-linked dextran gel (Sephadex ® G-100) with a specific buffer volume ($K_{av}$) corresponding to a molecular weight of 37,000, that it shows an isoelectric point of 3.0±0.2 as determined by isoelectric focusing, that its specific absorption in a 1% aqueous solution at 280 nm and 1 cm light path ($A_{1\,cm}^{280}$ 1%) amounts to 13.5±0.5, that it has a carbohydrate content of 20±3%, that, in a concentration of 1 μg/ml of test mixture, when incubated with a chromogenic substrate according to claim 5 or 6 at pH 7–8.5 and 37° C., it causes no absorbancy exceeding 0.01 per minute as measured at 405 nm and 1 cm light path, that, after intravenous administration to rabbits in a dose of 80 U per kg body weight, it prolongs at least twice the initial value of the activated partial thromboplastin time in plasma, that, after intravenous administration in a dose of 80 U per kg body weight, it causes no acute toxic symptoms and no behavioural disturbances in rabbits, that, upon repeated subcutaneous administration, it stimulates the formation of antibodies in rabbits whereby the antibody present in the serum of the rabbits immunized against the activator preparation forms together with the antigen a precipitating complex as evidenced by immunodiffusion.

The activator preparation can also be obtained from cultures of genetically homogeneous (cloned) microorganisms, such as Escherichia coli or Saccharomyces cerevisiae for instance, which acquired the ability of biosynthesis of protein C-activator by genetic manipulation.

The genetic transformation of the concerned microorganisms can be performed according to known methods, by recombination of their desoxyribonucleic acid (DNA) carrying the genetic information with a DNA-chain (gene) bearing the programme for the biosynthesis of protein C-activator.

To obtain genes bearing the programme for the biosynthesis of protein C-activator, either a DNA-chain can be synthesized according to the pattern of the primary structure of protein C-activator in such a way that its base sequence determines the amino acid sequence of the activator during its biosynthesis, but DNA-chains can also be modified by chemical interventions in such a way that the required base sequence is obtained, or natural genes bearing the programme for the biosynthesis of protein C-activator can be isolated from cells of snake species.

The basic principles of gene technology have been described by E. L. WINNACKER, "Gene und Klone", Weinheim, VCA-Verlag (1985).

The activator preparation of the invention is also capable of activating protein C in the living organism of vertebrates. By intravenously injecting the activator preparation into rabbits and by measuring the activated partial thromboplastin time in plasma samples of the test animals before and after the injection, a significant prolongation of the clotting time can be observed. This prolongation of the activated partial thromboplastin time has to be attributed to a destruction of the factors $V_a$ and $VIII_a$ during the coagulation process.

None of the animals showed signs of toxic effects of the activator preparation. These results indicate that the activator preparation of the invention may not only be used for assaying protein C but also for pharmacological investigations on protein C-effects in test animals. Moreover, this activator preparation can be used as an antithrombotically active drug in human and veterinary medicine.

Fresh, frozen or lyophilized blood plasma from men or mammals comprising the usual calcium ion-binding additives, such as citrate or oxalate, or plasma preparations from which inhibitors or components irrelevant to the protein C assay were removed by heating, pH adjustment or treatment with enzymes, adsorbing or protein-precipitating agents, can be used as natural substrates for measuring the action of activated protein C via inactivation of factors V and VIII in the clotting test. In addition, clotting factor concentrates from blood plasma or by-products thereof, which are applied for therapeutical purposes, and factor-deficient plasma can be used as well.

Oligopeptides, in particular di- or tripeptidyl-L-arginine derivatives, the C-terminal arginine of which is attached to a chromogenic group through an amide bond capable of being enzymatically split off by activated protein C, as well as salts thereof with mineral or organic acids are appropriate as synthetic substrates for the direct photometric activity measurement of activated protein C.

Particularly compounds having the following formula can be used

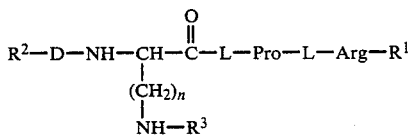

wherein n represents integer 3 or 4,
R² represents hydrogen, or
  (a) a straight or branched alkanoyl group having 2 to 6 carbon atoms,
  (b) an ω-carboxyl, ω-methoxycarbonyl or ω-ethoxycarbonyl-alkanoyl group having 2 to 4 carbon atoms in the alkanoyl,
  (c) a straight or branched alkoxycarbonyl group having 1 to 4 carbon atoms in the alkoxy,
  (d) an alkylsulfonyl group having 1 to 2 carbon atoms in the alkyl,
  (e) an unsubstituted or substituted benzoyl group, or
  (f) a benzyloxycarbonyl group the nucleus of which is unsubstituted or substituted,
R³ represents hydrogen, or a group as defined for R² according to (a) to (f), and besides represents an amidino or tosylamidino group, if n=3, and R¹ represents a p-nitrophenylamino, 1- or 2-naphthylamino, 4-methoxy-2-naphthylamino, 4-methylcoumaryl-(7)-amino, 1,3-di(methoxycarbonyl)-phenyl-(5)-amino, chinonylamino or nitrochinonylamino group, and salts thereof with a mineral or an organic acid.

As examples of such synthetic substrates, H—D—Pro—L—Pro—L—Arg-pNA, D—Pyroglu—L—Pro—L—Arg—pNA, H—D—Lys (ε—Cbo)—L—Pro—L—Arg—pNA, H—D—Lys—L—Pro—L—Arg—pNA and salts thereof, in particular hydrochlorides and acetates, can be mentioned.

As the protein C-activating activator preparation of the invention (snake venom protein), in contrast to thrombin, does not exert any detectable proteinase activity and therefore is not capable of splitting any synthetic protein C-substrate, those substrates which cannot be applied with the usual photometric methods for assaying protein C in plasma because they are not only split off by activated protein C but also by the thrombin added for activation, can be used for assaying activated protein C according to the method of the invention.

The following compounds for example belong to this category of synthetic substrates: 2AcOH.H—D—CHG—L—Pro—L—Arg—pNA, 2AcOH.H—D—CHG—L—Ala—L—Arg—pNA, Tos-Gly—L—Pro—L—Arg—pNA.AcOH and phenylsulfonyl—Gly—L—Pro—L—Arg—pNA.AcOH.

The abbreviations used in the above formulas have the following meaning: Ala=alanine; Arg=arginine; Cbo=carbobenzoxy; CHG=cyclohexylglycine; Lys=lysine; pNA=p-nitroanilide; Pro=proline; Pyroglu=pyroglutamin acid.

Moreover, the method of the invention allows to assay quantitatively the activity of protein C-inhibitors by adding the inhibitor-containing sample to a known quantity of protein C, by converting protein C into activated protein C with the activator preparation, by determining the non-inhibited protein $C_a$-activity by means of a synthetic or natural substrate after an adequate reaction time and by calculating the inhibitor content from the difference between the initial and the remaining protein $C_a$-activity.

In addition, it has been found that the activator preparation covalently bound to an insoluble support is capable of activating protein C in protein C-containing media and, that it may, after accomplished activation, be removed easily and totally from the aqueous medium, thus allowing the use of an insolubilized activator preparation for obtaining activated protein C. For instance, plasma and plasma fractions of men and mammals, extracts of human placenta as well as culture liquids and extracts of cultures of prokaryontic and eukaryontic cells capable of producing protein C may be used as protein C-containing media. For the purpose of insolubilization, the protein C activator can be bound e.g. to CNBr-sepharose, putrescinagarose or epsilonaminocaproylagarose according to known methods (R. SCOPES, Protein Purification, Principles and Practice, p. 113–117, New York, Heidelberg, Berlin: Springer Verlag (1982)).

The activation of protein C by the insolubilized activator preparation may be performed either by batchwise stirring or by using a column provided with the insolubilized activator, in a continuous process. The isolation and purification of activated protein C can be carried out according to known methods (W. KISIEL and E. W. DAVIE, Protein C, Methods in Enzymology 80, 320–332 (1981)).

EXAMPLE 1

Manufacture of a protein C activator preparation from A. contortrix venom 200 mg of Agkistrodon contortrix venom were dissolved in 1 ml of 0.015M sodium phosphate buffer, pH 6.8, centrifuged and the supernatent applied on a DEAE-Sephadex ® A-50 column (cross-linked diethylaminoethyldextran) of 2.6×90 cm equilibrated with the same buffer. Thereafter, it was eluted with a linear gradient mixed of 0.015M sodium phosphate buffer, pH 6.8, and of 0.4M sodium chloride in 0.015M sodium phosphate buffer, pH 6.8, and fractions of 20 ml were collected. The protein C-activating action of the individual fractions was assayed by incubating commercial barium citrate eluate from human plasma, 1 mU per ml (Plasma Barium Citrate Eluate, Sigma-Chemie GmbH, Munich, FRG) with the sample during 15 minutes at 37° C., by pipetting 0.1 ml thereof into 0.1 ml of human normal plasma, by adding to this mixture at 37° C. 0.1 ml of kephalin-ellagic acid reagent (Actin ®, Dade, Aguada, Puerto Rico, USA) and 0.1 ml of 0.025M calcium chloride, by starting a chronometer and by measuring the time until coagulation. The protein C activator-containing samples caused a prolongation of the clotting time from 34 seconds (control without eluate) to 60 to 90 seconds according to the activator content.

The protein C-activating activity was contained in the fractions 40–45 (see figure enclosed). The pooled active eluates from 8 chromatography batches were concentrated by ultrafiltration, desalted, dissolved in 0.1M glycine pH 7.4 and lyophilized. 830 mg of lyophilizate with a protein content of 16.5% were obtained.

5 µg of the obtained activator preparation (0.825 µg of protein) caused maximum activation of 40 mU of purified human protein C at 37° C. and pH 8.0 within 7.5 minutes, measured on the synthetic chromogenic substrate 2AcOH.H—D—Pro—L—Pro—L—Arg—pNA.

EXAMPLE 2

Photometric assay of purified protein C

A series of dilutions was prepared with 0.1M Tris-HCl buffer, pH 8.0, from a stock solution of human protein C with a protein content of 1.1 mg per ml, which was isolated and purified by barium citrate adsorption and subsequent elution, chromatography on cross-linked diethylaminoethylagarose, chromatography on dextran sulphate agarose and preparative polyacrylamide gel electrophoresis.

The protein C content of these dilutions was determined by adding 0.010 ml of protein C dilution in a photometer cuvette to 0.200 ml of a protein C-activator solution of 0.025 mg/ml, prepared according to Example 1, by incubating this mixture for 7.5 minutes at 37° C., by adding 1.390 ml of Tris-imidazole buffer, pH 8.4, ionic strength 0.3, and 0.400 ml of the chromogenic substrate 2AcOH.H—D—Pro—L—Pro—L—Arg—pNA, 4 µmoles per ml, and by recording continuously at 405 nm the increase in absorbance ($\Delta A$) caused by the released p-nitroaniline.

The protein C content of the sample was calculated from the increase in absorbance per time unit by means of the following equation:

$$\frac{\Delta A/\text{min} \cdot V}{v \cdot \epsilon} = U/\text{ml sample}$$

V = test volume
v = sample volume
$\epsilon$ = millimolar extinction coefficient of p-nitroaniline
U = international enzyme unit, quantity of enzyme which converts 1 µmole of substrate per minute under standard conditions.

The measured substrate hydrolysis due to activated protein C is proportional to the protein C content of the sample (see table 1).

TABLE 1

| Photometric assay of purified protein C | | |
|---|---|---|
| µl protein C stock solution | $\Delta A$/min | U protein C per ml stock solution |
| 10 | 0.080 | 16.1 |
| 12 | 0.098 | 16.4 |
| 15 | 0.126 | 16.9 |
| 18 | 0.152 | 16.9 |

TABLE 1-continued

| Photometric assay of purified protein C | | |
|---|---|---|
| µl protein C stock solution | $\Delta A$/min | U protein C per ml stock solution |
| 20 | 0.166 | 16.6 |

EXAMPLE 13

Photometric assay of protein C in plasma

The protein C content of human citrated plasma was assayed by adding 0.050 ml of plasma in a photometer cuvette to 0.200 ml of protein C activator (prepared according to Example 1, 0.025 mg/ml), by incubating this mixture for 7.5 minutes at 37° C., by adding 1.550 ml of Tris-imidazole buffer, pH 8.4, ionic strength 0.3, and 0.200 ml of the chromogenic substrate 2AcOH.-H—D—CHG—L—Pro—L—Arg—pNA, 4 µmoles/ml, and by recording continuously at 405 nm the absorption increase caused by the released p-nitroaniline.

A protein C content of 0.90 U per ml of plasma could be calculated with the formula mentioned in Example 2.

EXAMPLE 4

Determination of protein C in plasma with a clotting method 0.1 ml of reagent for determining the activated partial thromboplastin time (Actin ®, DADE, Aguada, Puerto Rico, USA), 0.1 ml of plasma and 0.1 ml of the activator prepared according to Example 1 (200 µg/ml) were incubated for 60 seconds at 37° C., 0.1 ml of calcium chloride solution 0.025M was added and the time until coagulation was measured by means of a chronometer.

As a model for protein C-dificient plasma, different doses of a commercial anti-protein C antibody-preparation (Merz and Dade, Düdingen, CH) were added to normal plasma.

The coagulation of normal plasma is prolonged by a multiple by the protein C activation; addition of anti-protein C leads to a dose-dependent reduction of the clotting time (Table 2).

TABLE 2

| Plasma (ml) | Protein C activator (ml) | Anti-protein C (µl) | Clotting time (seconds) |
|---|---|---|---|
| 0.1 | — | — | 35.5 |
| 0.1 | 0.1 | — | 140.5 |
| 0.1 | 0.1 | 2.5 | 108.0 |
| 0.1 | 0.1 | 5.0 | 79.5 |
| 0.1 | 0.1 | 10.0 | 51.5 |

EXAMPLE 5

100 mg of the activator prepared according to Example 1 were dissolved in 100 ml of physiological saline, the pH was adjusted to 7.4 with NaOH 1N and the solution was sterilized by filtration through a membrane filter having a pore size of 0.22µ.

1 ml of this solution per Kg body weight was injected intravenously into each of three rabbits. The activated partial thromboplastin time was measured in plasma samples of the test animals before and 30 minutes after the injection. An important prolongation of the clotting time could be observed in each animal; none of them showed symptoms of toxic effects.

The results of this test are shown in Table 3.

TABLE 3

| Animal Nr. | Activated partial thromboplastin time (sec.) | |
|---|---|---|
| | before injection | 30 min. after injection |
| 1 | 12.5 | 125 |
| 2 | 24 | 150 |
| 3 | 19.5 | 60 |

EXAMPLE 6

Manufacture of a highly purified protein C-activator preparation from A. contortrix venom 1 g of A. contortrix venom was dissolved in 100 ml of water,a the pH of this solution was adjusted to 3.0 with o-phosphoric acid 1N and the acid venom solution was kept 10 minutes in a water bath at 70±2° C., then cooled to 20° C., the pH adjusted to 7.2 with sodium hydroxide solution 1N, the turbid solution centrifuged and the residue diluted to a volume of 100 ml with distilled water in order to obtain a pre-purified venom fraction.

The pre-purified venom fraction was applied on a column with DEAE-Sephadex® A-50 of 2.6×90 cm equilibrated with 0.015M sodium phosphate buffer pH 6.8, eluted with a linear gradient mixed of 0.015M sodium phosphate buffer pH 6.8 and of 0.4M sodium chloride in 0.015M sodium phosphate buffer pH 6.8 and fractions of 20 ml were collected. The protein C-activating action of the individual fractions was assayed by mixing 0.1 ml of human citrated plasma, 0.1 ml of sample (diluted 1:350 in water), 0.1 ml of cephalin-ellagic acid reagent (Actin®) and 0.1 ml of calcium chloride solution 0.025M, by starting a chronometer and by measuring the time until coagulation. The protein C activator-containing samples caused a prolongation of the clotting time from 34 seconds to 200 seconds, according to the activator content.

The protein C-activating fractions were pooled, concentrated to 1/10 of the eluate volume by ultra-filtration, dissolved in sodium acetate buffer 0.05M pH 5.0 and adjusted to 100 ml, applied on a column of CM-Sephadex® C-50 equilibrated with sodium acetate buffer 0.05M pH 5.0, eluted with a linear gradient mixed of sodium acetate buffer 0.05M pH 5.0 and of sodium chloride 0.04M pH 5.0 in sodium acetate buffer 0.05M pH 5.0 and fractions of 20 ml, which were tested on protein C-activating action according to the above mentioned method, were collected.

The protein C-activating fractions were pooled, concentrated to 1/25 of their volume by ultrafiltration, adjusted to 25 ml with acetic acid 1% in dist. water and applied on a column of Sephadex® G-100 equilibrated with acetic acid 1% in water, eluted with acetic acid 1%, and fractions of 20 ml, which were again tested on protein C-activating action according to the previously mentioned method, were collected.

The protein C-activating fractions were pooled and lyophilized. A salt-free activator preparation which showed a single band in polyacrylamide gel electrophoresis and a protein C-activating activity of 35 U per mg, was obtained.

One unit (U) of protein C-activator is that quantity which completely activates the quantity of protein C present in 1 ml of normal citrated human plasma under standard conditions.

EXAMPLE 7

Production of activated protein C 25 mg of activator preparation according to Example 6 were dissolved in 100 ml of 0.1 molar sodium bicarbonate buffer, pH 8.3, 0.5 molar on NaCl. 5 g of CNBr-sepharose 4B (AB Pharmacia, Uppsala, S), first washed in 0.001N hydrochloric acid, were added to the solution. The mixture was stirred at 20°-25° C. for 2 hours. After complete reaction, the mixture was filtered through a glass suction filter G3 and the filtered insolubilized activator preparation was washed five times with 30 ml of sodium bicarbonate buffer of the above composition. To saturate the possibly present reactive CNBr-groups, the insolubilized activator preparation was stirred for 2 hours with 100 ml of 0.5% ethanolamine in sodium bicarbonate buffer of the above composition, collected again on a glass suction filter and washed still three times with 300 ml of sodium bicarbonate buffer.

One unit of barium sulphate eluate from human plasma (Sigma-Chemie GmbH, Munich, FRG), dissolved in 100 ml of distilled water, was filtered through a membrane filter with a pore size of 0.4μ. This solution, which had a protein C-content of 0.9 U per ml as measured with D—Lys(Cbo)—L—Pro—L—Arg—pNA, was added to the insolubilized activator preparation, stirred at room temperature for 2 hours and then filtered through a glass suction filter. The filtrate showed a content of 0.95 U of activated protein C.

We claim:

1. An activator preparation which is capable of converting the zymogen protein C of men and mammals into a proteinase with protein $C_a$-activity and which is obtainable from the venom of the snake Agkistrodon contortrix or from the venom of snake species which undergoes an immunological cross-reaction with the venom of Agkistrodon contortrix which comprises:

(a) chromatography on an anion exchanger having the appropriate porosity for binding proteins,
(b) elution with sodium phosphate buffer at neutral pH and increasing ionic strength,
(c) removal of electrolytes from the active fractions by ultrafiltration, and
(d) subsequent lyophilization.

2. An activator preparation which can be obtained in highly purified form which comprises:

(a) dilution of the venom of the snake Agkistrodon contortrix or from the venom of snake species which undergoes an immunological cross-reaction with the venom of Agkistrodon contortrix in an aqueous medium,
(b) removal of the undesired venom components from the solution either by fractionated alcohol precipitation, fractionated salt precipitation or heat treatment at an acid pH for the purposes of preparing a pre-purified venom fraction,
(c) further purification of the obtained prepurified venom fraction by chromatography on an anion exchanger having the appropriate porosity for binding proteins,
(d) elution with sodium phosphate buffer at neutral pH and increasing ionic strength,
(e) further chromatography on a cation exchanger,
(f) elution with a sodium acetate buffer at an acid pH,
(g) concentration of the protein C-activating eluates by ultrafiltration, (h) removal of electroloytes and final purification of the concentrate by chromatography on a molecular sieve gel using diluted aqueous acetic acid as the eluent, and (i) subsequent lyophilization.

3. An activator preparation which is capable of converting the zymogen protein C of men and mammals into a proteinase with protein $C_a$-activity comprising:

(a) culturing a cloned microorganism containing at least one gene bearing the program for the biosynthesis of protein C-activator from the venom of the snake Agkistrodon contortrix or from the venom of snake species which undergoes an immunological cross-reaction with the venom of Agkistrodon contortrix;

(B) isolating said protein C-activator from said culture.

4. An activator preparation composition for preventing or treating thrombotic disorders comprising a therapeutically effective amount of the activator preparation according to claim 1, 2 or 3 and a pharmaceutically acceptable carrier.

5. A method of preventing or treating thrombotic disorders in living organismsof vertebrates which comprises the administration to a living organism in need of said prevention or treatment a therapeutically effective amount of the activator preparation according to claim 1, 2 or 3.

6. A method for obtaining activated protein C from protein C-containing aqueous media, which comprises:

(a) binding the activator preparation according to claim 1, 2 or 3 to a water-insoluble support, for the purpose of insolubilization;

(b) reacting the insolubilized activator preparation with the protein C-containing aqueous medium for activating protein C;

(c) removing the insolubilized activator preparation from the aqueous medium after accomplished transformation of protein C into activated protein C; and (d) isolating the activated protein C from the aqueous media.

7. A method for quantitatively assaying protein C in a medium containing same, which comprises:

(A) reacting said medium with an activator preparation according to claim 1, 2, or 3 for a period of time sufficient to cause maximum activation of the zymogen protein C to a proteinase having protein $C_a$-activity, and (B) determining the quantity of activated protein C thus formed by:

(i) photometrically measuring the quantity of colored or fluorescent split product formed as a result of a catalytic hydrolytic action of activated protein C on a synthetic chromogenic peptide substrate having a chromogenic group susceptible of being enzymatically split off by activated protein C with formation of a colored or fluorescent compound, said quantity being proportional to the amount of protein C present in the test mixture, or (ii) measuring the prolongation of the clotting time of plasma or a plasma fraction caused by the proteolytic inactivation of plasma clotting factors V and V111 due to the catalytic action of activated protein C, the said prolongation being proportional to the amount of protein C in said medium.

8. A method for quantitatively assaying protein C in a medium containing the same which comprises:

(A) adding to said medium:

(a) a synthetic chromogenic peptide substrate having a chromogenic group susceptible of being enzymatically split off by activated protein C with formation of a colored or fluorescent compound; and (b) an activator preparation according to claim 1, 2, or 3, (B) following photometrically the hydrolytic release of the colored or fluorescent split product from said synthetic chromogenic peptide substrate having a chromogenic group susceptible of being enzymatically split off by activated protein C with formation of a colored or fluorescent compound and calculating the protein C content in said medium from the observed maximum velocity of the substrate hydrolysis.

9. A method according to claim 7 wherein said protein C containing medium is selected from the group consisting of: blood plasma or fractions thereof, solutions of purified protein C, eluates of protein C-adsorbates, organ extracts, filtrates of tissue cultures and extracts of tissue cultures, or culture liquids and extracts of cultures of genetically modified and protein C-producing microorganisms.

10. A method according to claim 7 which comprises using as said synthetic chromogenic peptide substrate an oligopeptide consisting of a di- or tripeptidyl—L—arginine, the C-terminal arginine of which is attached to a chromogenic group through an amide bond capable of being enzymatically split off by activated protein C.

11. A method according to claim 7 wherein said synthetic chromogenic substrate has the general formula:

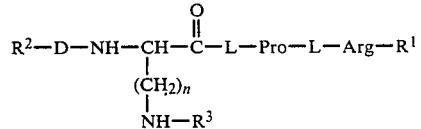

wherein:

n represents integer 3 or 4, $R^2$ represents hydrogen, or (a) a straight or branched alkanoyl group having 2 to 6 carbon atoms, an ω-carboxyl, ω-methoxycarbonyl or ω-ethoxycarbonylalkanoyl group having 2 to 4 carbon atoms in the alkanoyl, (c) a straight or branched alkoxycarbonyl group having 1 to 4 carbon atoms in the alkoxy, (d) an alkylsulfonyl group having 1 to 2 carbon atoms in the alkyl, (e) a benzoyl group, or (f) a benzyloxycarbonyl group, $R^3$ represents hydrogen, or a group as defined for $R^2$ according to (a) to (f), and besides represents an amino or tosyl-amidino group, if n=3, and $R^1$ represents a p-nitrophenylamino, 1- or 2-naphthylamino, 4-methoxy-2-naphthylamino, 4-methylcoumaryl-(7)-amino, 1,3-di-(methoxycarbonyl)-phenyl-(5)-amino, chinonylamino or nitrochinonylamino group, or salts thereof with a mineral or an organic acid.

12. A method according to claim 7 wherein said synthetic chromogenic peptide substrate is selected from the group consisting of: H—D—Pro—L—Pro—L—Arg—pNA, L—pyroglu—L—Pro—L—Arg—pNA, H—D—Lys(ε-Cbo)—L—Pro—L—Arg—pNA and H—D—Lys—L—Pro—L—Arg—pNA.

13. A method according to claim 7 wherein said synthetic chromogenic peptide substrate is selected from the group consisting of: 2AcOH.H—D—CHG—L—Pro—L—Arg—pNA and 2AcoH.H—D—CHG—L—Ala—L—Arg—pNA.

14. A method according to claim 8 wherein said protein C containing medium is selected from the group consisting of: blood plasma or fractions thereof, solutions of purified protein C, eluates of protein C-adsorbates, organ extracts, filtrates of tissue cultures and extracts of tissue cultures, or culture liquids and extracts of cultures of genetically modified and protein C-producing microorganisms.

15. A method according to claim 8 which comprises using as said synthetic chromogenic peptide substrate an oligopeptide consisting of a di- or tripeptidyl—L—arginine, the C-terminal arginine of which is attached to a chromogenic group through an amide bond capable of being enzymatically split off by activated protein C.

16. A method according to claim 8 wherein said synthetic chromogenic substrate has the general formula:

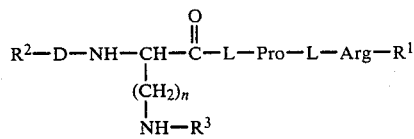

wherein:
n represents integer 3 or 4,
R² represents hydrogen, or
  (a) a straight or branched alkanoyl group having 2 to 6 carbon atoms,
  (b) an ω-carboxyl, ω-methoxycarbonyl or ω-ethoxycarbonylalkanoyl group having 2 to 4 carbon atoms in the alkanoyl,
  (c) a straight or branched alkoxycarbonyl group having 1 to 4 carbon atoms in the alkoxy,
  (d) an alkylsulfonyl group having 1 to 2 carbon atoms in the alkyl,
  (e) a benzoyl group, or
  (f) a benzyloxycarbonyl group,
R³ represents hydrogen, or a group as defined for R² according to (a) to (f), and besides represents an amino or tosyl-amidino group, if n=3, and
R¹ represents a p-nitrophenylamino, 1- or 2-naphthylamino, 4-methoxy-2-naphthylamino, 4-methylcoumaryl-(7)-amino, 1,3-di-(methoxycarbonyl)-phenyl-(5)-amino, chinonylamino or nitrochinonylamino group, or salts thereof with a mineral or an organic acid.

17. A method according to claim 8 wherein said synthetic chromogenic peptide substrate is selected from the group consisting of: H—D—Pro—L—Pro—L—Arg—pNA, L—pyroglu—L—Pro—L—Arg—pNA, H—D—Lys(ε—Cbo)—L—Pro—L—Arg—pNA and H—D—Lys—L—Pro—L—Arg—pNA.

18. A method according to claim 8 wherein said synthetic chromogenic peptide substrate is selected from the group consisting of: 2AcOH.H—D—CHG—L—Pro—L—Arg—pNA and 2AcoH.H—D—CHG—L—Ala—L—Arg—pNA.

* * * * *

UNITED STATES PATENT AND TRADEMARK OFFICE
CERTIFICATE OF CORRECTION

PATENT NO. : 4,849,403

DATED : July 18, 1989

INVENTOR(S) : Kurt F. Stocker, et al.

It is certified that error appears in the above-identified patent and that said Letters Patent is hereby corrected as shown below:

Title page, item [30]:

In the Foreign Application Priority Data section of the caption, change "4135/84" to -- 4135/85 --.

Signed and Sealed this

Third Day of April, 1990

Attest:

HARRY F. MANBECK, JR.

*Attesting Officer*     *Commissioner of Patents and Trademarks*